(12) United States Patent
Eliason et al.

(10) Patent No.: US 9,131,874 B2
(45) Date of Patent: Sep. 15, 2015

(54) FLUOROSCOPY-INDEPENDENT, ENDOVASCULAR AORTIC OCCLUSION SYSTEM

(75) Inventors: Jonathan L. Eliason, Ann Arbor, MI (US); Todd E. Rasmussen, Fair Oaks Ranch, TX (US)

(73) Assignees: THE REGENTS OF THE UNIVERSITY OF MICHIGAN, Ann Arbor, MI (US); The United States of America as represented by the Secretary of the Air Force, Washington, DC (US)

( * ) Notice: Subject to any disclaimer, the term of this patent is extended or adjusted under 35 U.S.C. 154(b) by 310 days.

(21) Appl. No.: 13/642,465

(22) PCT Filed: Apr. 21, 2011

(86) PCT No.: PCT/US2011/033368
§ 371 (c)(1),
(2), (4) Date: Jan. 7, 2013

(87) PCT Pub. No.: WO2011/133736
PCT Pub. Date: Oct. 27, 2011

(65) Prior Publication Data
US 2013/0102926 A1    Apr. 25, 2013

Related U.S. Application Data

(60) Provisional application No. 61/326,478, filed on Apr. 21, 2010.

(51) Int. Cl.
*A61B 5/107* (2006.01)
*A61M 25/04* (2006.01)
(Continued)

(52) U.S. Cl.
CPC ............. *A61B 5/1076* (2013.01); *A61B 5/6851* (2013.01); *A61B 17/12031* (2013.01);
(Continued)

(58) Field of Classification Search
CPC .... A61B 5/107; A61B 5/1072; A61B 5/1075; A61B 10/00; A61B 2010/009; A61B 2025/1052; G01B 3/1084; B42D 15/00; B42D 15/0086
USPC ................... 600/587; 128/897, 898; 606/194; 33/511, 512, 700, 701, 732, 759–761; 73/866.3; 283/67, 70, 115, 117, 900; 434/187, 262–275
See application file for complete search history.

(56) References Cited

U.S. PATENT DOCUMENTS 2,156,289 A * 5/1939 Hoy ................................ 346/21
4,713,888 A * 12/1987 Broselow ......................... 33/512
(Continued)

FOREIGN PATENT DOCUMENTS

WO   WO-2004049970 A3   8/2004
WO   WO-2007022592 A1   3/2007
(Continued)

OTHER PUBLICATIONS

Sandgren, et al. "The diameter of the common femoral artery in healthy human: influence of sex, age, and body size." Journal of vascular surgery 29.3 (1999): 503-510. Retrieved from <http://www.sciencedirect.com/science/article/pii/S074152149970279X> on Oct. 14, 2014.*
(Continued)

*Primary Examiner* — Devin Henson
*Assistant Examiner* — David J McCrosky
(74) *Attorney, Agent, or Firm* — Marshall, Gerstein & Borun LLP

(57) ABSTRACT

A system for deploying and selectively inflating a thoracic aortic balloon at a desired location within the thoracic aorta for resuscitative aortic occlusion, inferior to the left subclavian artery, without the aid of fluoroscopy is described. Using CT imaging data, a distance between readily identifiable and consistently located external landmarks of torso extent is measured. Next, using the same data, a second distance from the femoral artery to a desired aortic occlusion location inferior to the left subclavian artery is determined. A correlation between the external measure of torso extent and the desired intra-arterial (i.e. endovascular) distance within the torso is made. Using a nomogram, a calibrated endovascular resuscitative thoracic aortic occlusion system can be positioned to this desired location on any injured individual with end-stage shock and impending cardiovascular collapse or death without the aid of fluoroscopy for delivery or balloon inflation.

6 Claims, 14 Drawing Sheets

(51) Int. Cl.
  *A61M 25/09* (2006.01)
  *A61B 5/00* (2006.01)
  *A61B 17/12* (2006.01)
  *B42D 15/00* (2006.01)
  *G01B 3/10* (2006.01)
  *A61M 25/00* (2006.01)
  *A61M 25/10* (2013.01)

(52) U.S. Cl.
  CPC ............... *A61M25/04* (2013.01); *A61M 25/09* (2013.01); *A61B 5/1072* (2013.01); *A61B 5/1075* (2013.01); *A61M 2025/0008* (2013.01); *A61M 2025/0081* (2013.01); *A61M 2025/09183* (2013.01); *A61M 2025/1052* (2013.01); *B42D 15/0006* (2013.01); *B42D 15/0086* (2013.01); *G01B 3/1084* (2013.01)

(56) References Cited

U.S. PATENT DOCUMENTS

| | | | | |
|---|---|---|---|---|
| 4,823,469 | A * | 4/1989 | Broselow | 33/760 |
| 4,865,549 | A * | 9/1989 | Sonsteby | 434/262 |
| 4,926,885 | A * | 5/1990 | Hinkle | 128/898 |
| 5,738,652 | A | 4/1998 | Boyd et al. | |
| 5,911,702 | A * | 6/1999 | Romley et al. | 604/509 |
| 6,453,572 | B2 * | 9/2002 | Cross et al. | 33/563 |
| 6,719,720 | B1 | 4/2004 | Voelker et al. | |
| 7,434,326 | B2 * | 10/2008 | Gifford | 33/528 |
| 2008/0027356 | A1 * | 1/2008 | Chen et al. | 600/587 |
| 2008/0082119 | A1 * | 4/2008 | Vitullo | 606/192 |
| 2009/0062666 | A1 * | 3/2009 | Roteliuk | 600/485 |
| 2009/0265951 | A1 * | 10/2009 | Black | 33/759 |
| 2010/0016735 | A1 * | 1/2010 | Harpas et al. | 600/485 |
| 2010/0041984 | A1 | 2/2010 | Shapland et al. | |

FOREIGN PATENT DOCUMENTS

| WO | WO-2008013441 A1 | 1/2008 |
|---|---|---|
| WO | WO-2006135853 A3 | 4/2009 |

OTHER PUBLICATIONS

Sam II, et al. "Blunt traumatic aortic transection: endoluminal repair with commercially available aortic cuffs." Journal of vascular surgery 38.5 (2003): 1132-1135. Retrieved from <http://www.sciencedirect.com/science/article/pii/S0741521403007171> on Oct. 14, 2014.*

Peterson, et al. "Percutaneous endovascular repair of blunt thoracic aortic transection." Journal of Trauma-Injury, Infection, and Critical Care 59.5 (2005): 1062-1065. Retrieved from <http://www.clubdelpercutaneo.org/pdf/Percutaneous%20Endovascular%20Repair%20of%20Blunt/%20Thoracic%20Aortic.pdf> on Oct. 14, 2014.*

Langewouters et al. "The static elastic properties of 45 human thoracic and 20 abdominal aortas in vitro and the parameters of a new model." J. Biomechanics 17.6 (1984): 425-435. Retrieved from <http://dspace.library.uu.nl/bitstream/handle/1874/25204/wesseling_84_the%20static%20elastic%20properties%20of%2045%20human.pdf> on Mar. 31, 2015.*

International Search Report and Written Opinion for PCT/US2011/033368 dated Oct. 14, 2011.

* cited by examiner

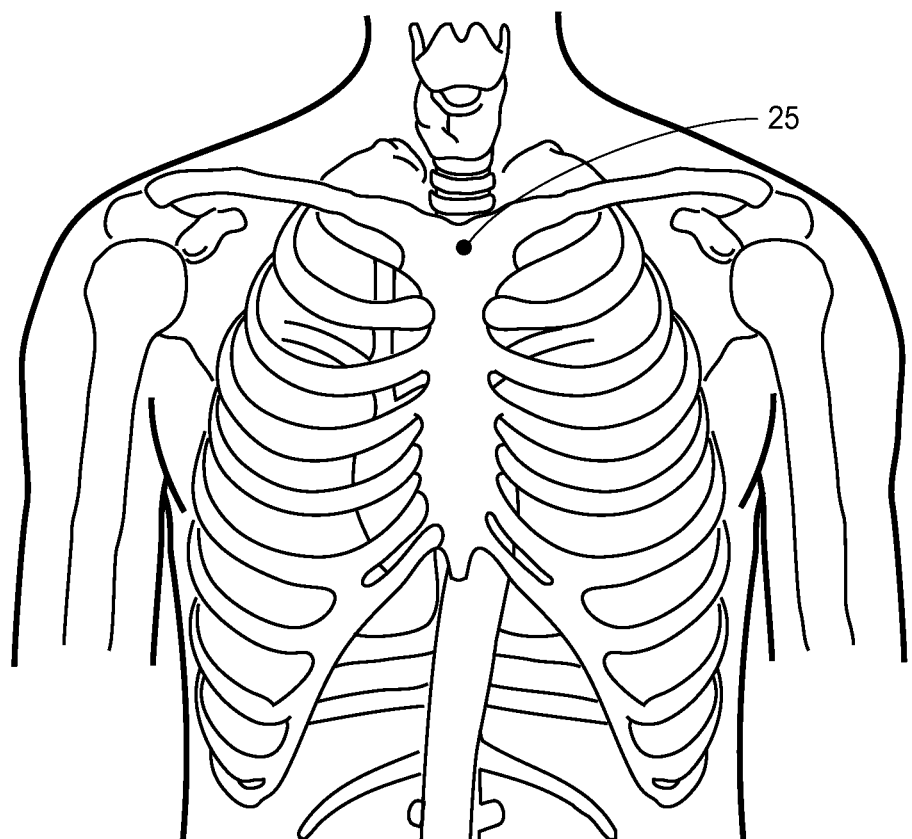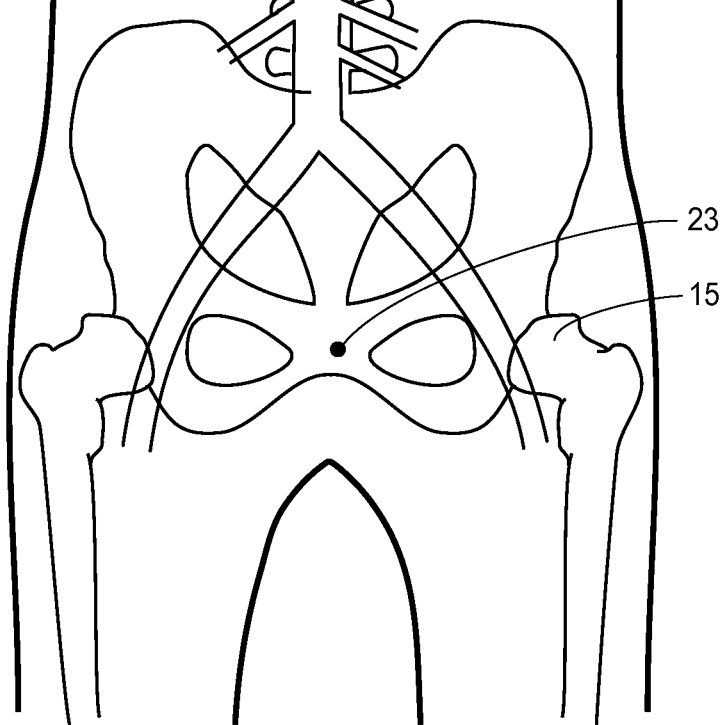
FIG. 1A

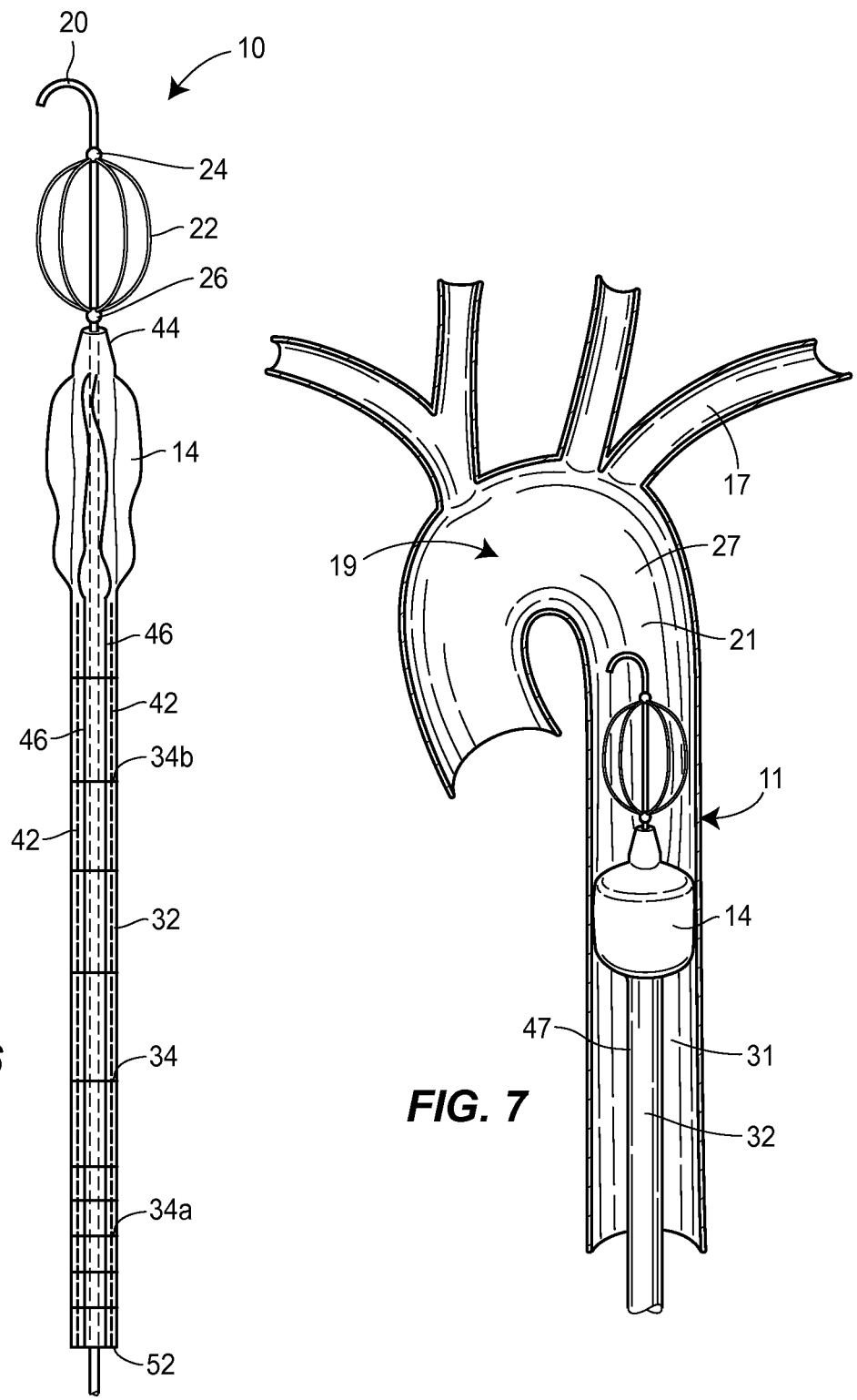

| Male Safe Zone Arterial Insertion Lengths/diam. | | | | Male Safe Zone Venous Insertion Lengths/diam. | | | |
|---|---|---|---|---|---|---|---|
| Torso Extent In cm | CIA Zone | Infrarenal Aortic Zone | Thoracic Aortic Zone | Torso Extent In cm | CIV Zone | Infrarenal IVC Zone | Retrohepotic IVC Zone |
| 35 | 18/7.7 | 26/16.1 | 42/18.5 | 35 | 17/8.5 | 24/22.1 | 38/26.3 |
| 36 | 18 | 26 | 42 | 36 | 17 | 24 | 38 |
| 37 | 18 | 26 | 42 | 37 | 17 | 24 | 38 |
| 38 | 18 | 26 | 43 | 38 | 18 | 24 | 39 |
| 39 | 18 | 27 | 43 | 39 | 18 | 24 | 39 |
| 40 | 19 | 27 | 43 | 40 | 18 | 24 | 39 |
| 41 | 19 | 27 | 44 | 41 | 18 | 25 | 39 |
| 42 | 19 | 27 | 44 | 42 | 18 | 25 | 39 |
| 43 | 19 | 28 | 44 | 43 | 18 | 25 | 39 |
| 44 | 19 | 28 | 45 | 44 | 18 | 25 | 40 |
| 45 | 20 | 28 | 45 | 45 | 18 | 26 | 40 |
| 46 | 20 | 28 | 45 | 46 | 18 | 26 | 40 |
| 47 | 20 | 29 | 46 | 47 | 19 | 26 | 40 |
| 48 | 20 | 29 | 46 | 48 | 19 | 26 | 40 |
| 49 | 20 | 29 | 46 | 49 | 19 | 26 | 40 |
| 50 | 21 | 29 | 47 | 50 | 19 | 26 | 41 |
| 51 | 21 | 30 | 47 | 51 | 19 | 27 | 41 |
| 52 | 21 | 30 | 47 | 52 | 20 | 27 | 41 |
| 53 | 21 | 30 | 48 | 53 | 20 | 27 | 41 |
| 54 | 21 | 30 | 48 | 54 | 20 | 27 | 41 |
| 55 | 22 | 31 | 48 | 55 | 20 | 27 | 41 |
| 56 | 22 | 31 | 49 | 56 | 20 | 27 | 42 |
| 57 | 22 | 31 | 49 | 57 | 20 | 27 | 42 |
| 58 | 22 | 31 | 49 | 58 | 20 | 28 | 42 |
| 59 | 22 | 32 | 50 | 59 | 20 | 28 | 42 |
| 60 | 23 | 32 | 50 | 60 | 20 | 28 | 42 |
| 61 | 23 | 32 | 50 | 61 | 21 | 28 | 42 |
| 62 | 23 | 32 | 51 | 62 | 21 | 28 | 43 |
| 63 | 23 | 33 | 51 | 63 | 21 | 28 | 43 |
| 64 | 23 | 33 | 52 | 64 | 21 | 29 | 43 |
| 65 | 23 | 33 | 52 | 65 | 21 | 29 | 43 |

Applicable Devices
• Arterial balloons
• Arterial filters
• TBD

Device Specifications
• Arterial balloons (xx mm)
• Arterial filters ()
• TBD

FIG. 15

| Female Safe Zone Arterial Insertion Lengths/diam. | | | | Female Safe Zone Venous Insertion Lengths/diam. | | | |
|---|---|---|---|---|---|---|---|
| Torso Extent In cm | CIA Zone | Infrarenal Aortic Zone | Thoracic Aortic Zone | Torso Extent In cm | CIV Zone | Infrarenal IVC Zone | Retrohepotic IVC Zone |
| 28 | 16/6.8 | 23/14.1 | 30/16.5 | 28 | 14/8.0 | 22/19.1 | 34/23.3 |
| 29 | 16 | 23 | 38 | 29 | 14 | 22 | 34 |
| 30 | 17 | 23 | 39 | 30 | 15 | 23 | 35 |
| 31 | 17 | 24 | 39 | 31 | 15 | 23 | 35 |
| 32 | 17 | 24 | 40 | 32 | 16 | 24 | 36 |
| 33 | 18 | 25 | 40 | 33 | 16 | 24 | 36 |
| 34 | 18 | 25 | 41 | 34 | 17 | 25 | 37 |
| 35 | 18 | 25 | 41 | 35 | 17 | 25 | 37 |
| 36 | 19 | 26 | 42 | 36 | 18 | 25 | 38 |
| 37 | 19 | 26 | 42 | 37 | 18 | 25 | 38 |
| 38 | 19 | 27 | 43 | 38 | 18 | 26 | 39 |
| 39 | 20 | 27 | 43 | 39 | 18 | 26 | 39 |
| 40 | 20 | 28 | 44 | 40 | 19 | 26 | 40 |
| 41 | 20 | 28 | 44 | 41 | 19 | 26 | 40 |
| 42 | 20 | 29 | 45 | 42 | 19 | 26 | 40 |
| 43 | 21 | 29 | 45 | 43 | 19 | 26 | 41 |
| 44 | 21 | 30 | 46 | 44 | 19 | 27 | 41 |
| 45 | 21 | 30 | 46 | 45 | 20 | 27 | 41 |
| 46 | 21 | 30 | 47 | 46 | 20 | 27 | 41 |
| 47 | 21 | 30 | 47 | 47 | 20 | 27 | 41 |
| 48 | 22 | 31 | 48 | 48 | 20 | 27 | 41 |
| 49 | 22 | 31 | 48 | 49 | 20 | 27 | 42 |
| 50 | 22 | 31 | 49 | 50 | 20 | 27 | 42 |
| 51 | 22 | 31 | 49 | 51 | 20 | 28 | 42 |
| 52 | 22 | 32 | 50 | 52 | 20 | 28 | 42 |
| 53 | 23 | 32 | 50 | 53 | 20 | 28 | 42 |
| 54 | 23 | 32 | 50 | 54 | 21 | 28 | 42 |
| 55 | 23 | 32 | 51 | 55 | 21 | 28 | 43 |
| 56 | 23 | 33 | 51 | 56 | 21 | 28 | 43 |
| 57 | 23 | 33 | 52 | 57 | 21 | 29 | 43 |
| 58 | 23 | 33 | 52 | 58 | 21 | 29 | 43 |

Applicable Devices
• Arterial balloons
• Arterial filters
• TBD

Device Specifications
• Arterial balloons (xx mm)
• Arterial filters ()
• TBD

FIG. 16

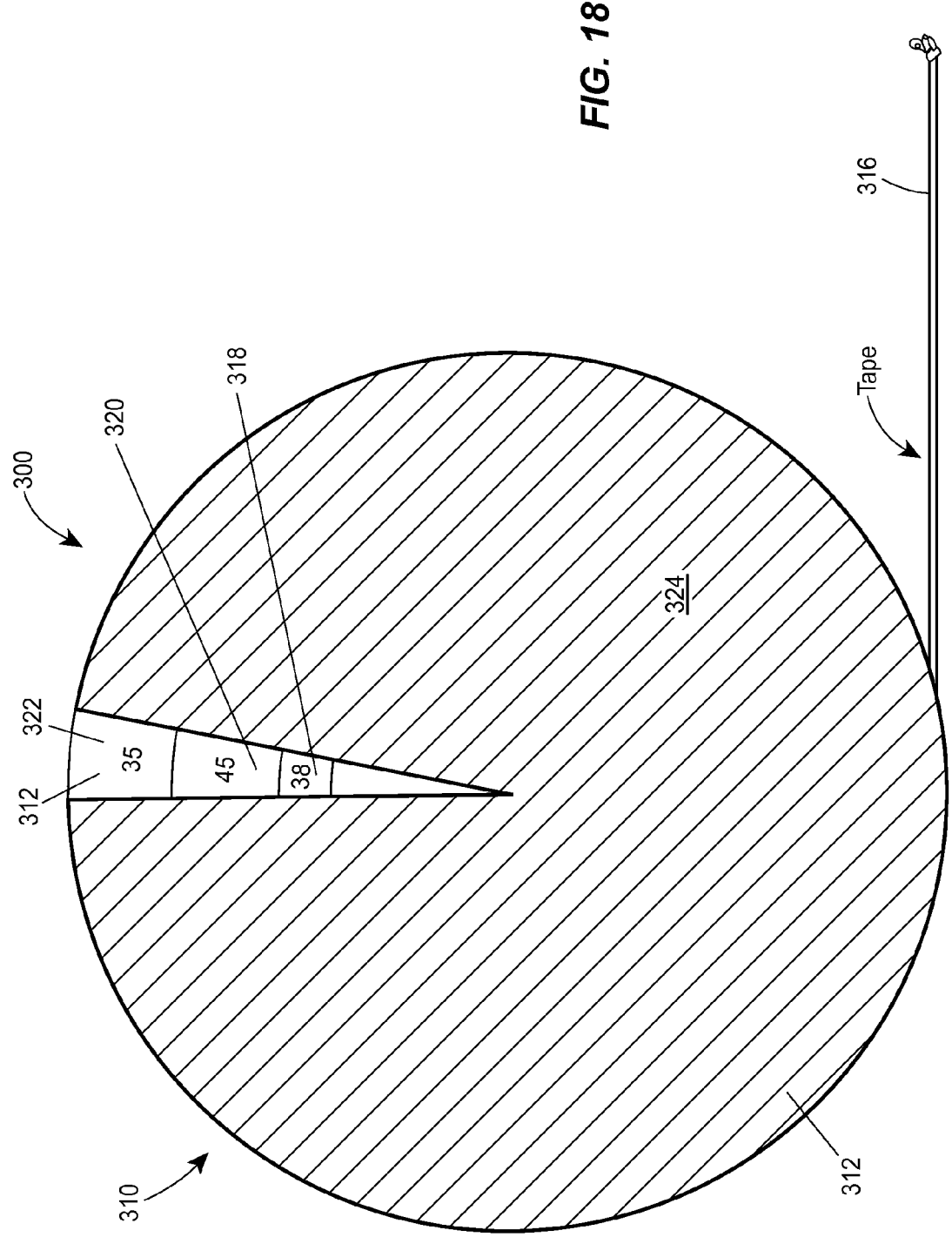

FLUOROSCOPY-INDEPENDENT, ENDOVASCULAR AORTIC OCCLUSION SYSTEM

CROSS-REFERENCE TO RELATED APPLICATIONS

This is a US national phase under 35 USC §371 of International Patent Application No. PCT/US2011/033368 filed Apr. 21, 2011, which claims the priority benefit of U.S. Provisional Application No. 61/326,478, the entire respective disclosures of which are incorporated herein by reference.

STATEMENT OF GOVERNMENT INTEREST

N/A.

FIELD OF THE DISCLOSURE

This disclosure relates generally to aortic occlusion systems deployed within the aorta, i.e. endovascular, used for resuscitation in the setting of profound shock from hemorrhage or cardiac or neurogenic causes resulting in severe central aortic hypotension and pending cardiovascular collapse. The injury patterns and scenario to which this system most applies, but to which this system is not limited, is torso or junctional hemorrhage not controllable with manual pressure or a tourniquet device, i.e. non-compressible hemorrhage. This disclosure relates further to endovascular resuscitative aortic occlusion systems that are applied rapidly in settings in which fluoroscopy is not available, i.e. fluoroscopy-independent, as a method of occluding the aorta and increasing central perfusion pressure to the heart and brain while controlling hemorrhage distal to the occlusion site.

BACKGROUND OF THE DISCLOSURE

Non-compressible sites of torso vascular injury remain one of the leading causes of potentially preventable death in both active duty troops during wartime conflict and in civilian trauma centers. An example of this type of torso vascular injury is a gunshot wound to the abdomen with a central site of bleeding and a patient in shock. Unlike an extremity injury, wherein a tourniquet could be used for vascular control or direct pressure could be held at select arterial pressure points, vascular injuries to the torso require surgical exposure followed by the often difficult application of vascular clamps for hemorrhage control. In a patient group presenting in shock, the time it takes to achieve such exposure and control may mean the difference between life and death. Specifically, the end stages of shock from hemorrhage or cardiac or neurologic causes are accompanied by critically low blood pressure and circulation to the brain and heart, which eventually lead to neurological death, cardiac arrest, or both.

Currently accepted methods of controlling hemorrhage in other areas of the body are not effective in treating torso hemorrhage. For example, while tourniquets have been developed and used successfully to manage bleeding from injured limbs, they are not successful in controlling torso bleeding. Manual pressure with and without new topical hemostatic agents and bandages has been taught for extremity and head and neck wounds, but is not successful for torso vascular injury. However, without similar expeditious maneuvers to address uncontrolled hemorrhage in the torso, this pattern of bleeding remains the leading cause of potentially preventable death on the modern battlefield and occurs frequently in civilian trauma centers.

Moreover, one currently acceptable method of managing non-compressible torso hemorrhage, i.e., open resuscitative thoracotomy with clamping of the thoracic aorta, has major limitations. For example, the performance of an emergency or resuscitative thoracotomy is maximally invasive as it involves a large opening of the left chest with retraction of the left lung and other vital structures to expose the thoracic aorta for clamping. As such, resuscitative thoracotomy requires specialized surgical instruments and lighting, and can only be performed by a select group of highly trained medical professionals. Patients undergoing this surgical maneuver require general anesthesia with endotracheal tube insertion and mechanical ventilation. If a thoracotomy with aortic cross-clamp placement is successful, the patient will have the added morbidity of an additional, large, cavitary wound from which to recover.

Thoracotomies are considered one of the most difficult surgical incisions to manage post-operatively, as they are extremely painful and frequently lead to lung complications. Chest wall pain and manipulation of the left lung from the procedure can prevent the patient from breathing effectively, and may lead to pneumonia. Notwithstanding these drawbacks, resuscitative thoracotomy is the only known and widely accepted method to control bleeding and support central blood pressure (i.e., perfusion to the heart and brain) in this setting. Acknowledged as an effort of last resort, this complex surgical maneuver is maintained as standard, despite the absence of significant tangible advances in the technique for the last four decades. Aside from refinements in determining which patients are best suited for this surgery, versus those in whom this is futile, the technique of occluding the thoracic aorta through an open incision, retracting the lung and clamping the aorta remains substantially the same in 2010 as it was in 1970. Further, the supporting literature demonstrates that survival associated with this surgery is less than 5%, considering all patients in whom it is performed.

Despite these substantial drawbacks, the fact that the surgical maneuver continues to be pursued, although old, suggests that the purpose behind the surgical maneuver, i.e., resuscitative thoracic aortic occlusion, has physiologic merit. The advantage of occluding the thoracic aorta in this setting is further substantiated by documented attempts at using rudimentary balloons within the thoracic aorta to accomplish this same result, i.e., occluding distal flow to the lower half of the body where the bleeding is occurring, and to support perfusion to the brain and myocardium. More specifically, use of a compliant balloon as a potentially effective treatment to emergency thoracotomy has been quietly explored for decades. The earliest reports describing this exploration in animal models were in the 1950s.

However, the technique of balloon occlusion in the thoracic aorta of young trauma victims was, and continues to be, inadequate because of deficient balloon design and the requirement for fluoroscopy in order to deploy any such devices. For example, currently marketed compliant occlusion balloons are available for use in ruptured aortic aneurysms, which by necessity has resulted in their extremely large diameter (up to 42 mm). Two examples of such aortic balloons are the Reliant (Medtronic Vascular), with a recommended delivery sheath of 12 French, and Coda (Cook Medical), with a recommended delivery sheath of 14 French. Each of these balloon systems require specialized and often scarce radiographic imaging (i.e. x-ray or fluoroscopy) to place and inflate them in the correct position in the thoracic aorta.

These large balloons require large diameter sheaths (12-14 French) which must be placed inside of the femoral and external iliac artery, and have not been designed for use specifically in the setting of non-compressible torso hemorrhage. In other words, the occlusion balloons have a large diameter design made for use in elderly individuals affected by aneurysm disease, and not for the normal aorta of young adult civilian trauma victims or injured military troops. Also, the delivery shafts of currently available balloons are too flexible to remain in position without a supporting sheath. As such, available occlusion balloons required very large and extended length sheaths in order to be delivered to and maintained or fixed at the desired position in the thoracic aorta.

Further, the balloons mentioned as examples above do not have a mechanism for safeguarding from over-inflation, which is why each must be inflated while being directly visualized using x-ray or fluoroscopy to prevent aortic rupture. For example, U.S. Pat. No. 6,719,720 discloses a two-balloon catheter system having a balloon-within-a-balloon that is designed to limit high arterial pressures to a defined location at the central site of ballooning. However, there is nothing that prevents over-pressurization of the internal aortic balloon.

The conventional technique of balloon occlusion is also limited by reliance upon x-ray or fluoroscopy to deliver and inflate the balloon within the correct position. For example, each of the balloons mentioned above can occlude an aorta, but each needs to be inflated under fluoroscopy to prevent aortic rupture. U.S. Pat. No. 5,738,652 discloses a catheter for use with inducing cardioplegic arrest in a patient that includes at its distal end a balloon "configured to occlude the coronary sinus of a patient's heart, and has a length and flexibility which allow the distal end to be positioned in the coronary sinus with the proximal end extending transluminally to a peripheral vein . . . and out of the body through a puncture therein." See U.S. Pat. No. 5,738,652 (Abstract). However, fluoroscopy is required to use this balloon catheter for such procedures. See U.S. Pat. No. 5,738,652, col. 4, lines 10-16 ("a body of clear fluid can be maintained in the aortic region upstream from the expanded distal end of the aortic catheter to facilitate imaging, e.g., angioscopic observation, of the cardiac procedure") and col. 8, lines 25-27 ("Shaft 122 is preferably radiopaque to permit fluoroscopic observation thereof to facilitate positioning."). Thus, the requirement of x-ray or fluoroscopy to use currently available balloon occlusion systems restricts performance of this procedure to fixed operating rooms with C-arm capabilities or fixed imaging suites, both of which are typically not available in trauma or emergency settings.

In addition to balloon occlusion, various other endovascular procedures are predicted on, or tied to, the use of real time fluoroscopy to visualize devices within the torso vessels. Although fluoroscopy affords visualization of endovascular procedures, the need for this modality carries a significant burden. Specifically, fluoroscopic imaging is costly and its requirement severely limits where catheter-based endovascular procedures can be performed and who can perform them. The requirement for fluoroscopy means that valuable and potentially lifesaving interventions can only be performed by a select number of trained providers in adequately equipped facilities often hours from a point of injury. Even routine or elective endovascular procedures may be delayed as they compete in a resource limited environment among a pool of procedures to be completed using fluoroscopic equipment in the intensive care unit, operating room or endovascular imaging suite. In addition, in emergency, intensive care or surgical environments, fluoroscopy is often not readily available or the environments in which the patients are positioned, e.g., an intensive care unit (ICU) bed or operating room (OR) table, are not specifically made for imaging, thereby impeding the use of fluoroscopy.

U.S. Pat. No. 4,713,888 to Broselow discloses a pediatric emergency tape that informs a physician of equipment lengths and sizes to perform emergency resuscitation on a child. The tape also provides references at each weight zone on the tape corresponding to pre-calculated medication dosages. However, there is no similar device for adult torso vascular anatomy, i.e. morphometry, which will facilitate or guide endovascular procedures of the torso.

In sum, existing and related technologies differ from the system and method of the present disclosure in function and form. Regarding function, current technologies were designed and approved for use in the temporary occlusion of large blood vessels, or to expand vascular prostheses (e.g., endovascular stent grafts in the elderly). In form, however, current related technologies were designed and approved for use with fluoroscopy, for both device positioning and device inflation. In contrast, the system and method of the present disclosure are designed specifically for use in a young adult population exposed to non-compressible torso hemorrhage from trauma or other forms of cardiogenic or neurogenic shock, who have normal aortic diameters, and importantly, without dependence on fluoroscopy.

SUMMARY OF THE DISCLOSURE

Using a sufficiently broad pool of human patients from which statistically reliable data may be drawn, it is possible to mathematically derive a correlation (i.e., nomogram) between readily measurable external torso landmarks and the dimensions of the human aorta within the abdomen and thorax. As used herein, the term nomogram includes one or more tables, charts, graphs, or other visual depiction of a correlation of data. More specifically, it is possible to define, using this easily discernable and consistently located external measure of torso extent, the anticipated lengths or distances of arterial anatomy, i.e. arterial morphometry, between functionally important locations within the torso. This mathematical correlation or nomogram will allow determination of the appropriate distance with which to insert an endovascular wire and aortic occlusion balloon into the torso aorta without the need for fluoroscopy (x-ray). In other words, the nomogram will allow a rapid measure of external torso extent in an injured individual or in an individual suffering from cardiogenic or neurogenic shock which will then provide the correlating distance to which the endovascular wire and resuscitative aortic occlusion balloon should be inserted. The endovascular wire and resuscitative aortic occlusion balloon are inserted through a puncture in the femoral artery to the standard location below the left subclavian artery at which point inflation of the balloon and occlusion of the aorta can be accomplished. The system of the present disclosure employs such data and provides a self-centering endovascular wire having a J tip sheath, introduced through a transdermal or percutaneous sheath (bridging the skin and subcutaneous tissue) to the torso arterial tree at the femoral artery, to deliver a sufficiently compliant aortic occlusion balloon to a location within the thoracic aorta below the left subclavian artery at the aortic arch. This technology enables aortic occlusion to augment heart and brain perfusion in response to non-compressible torso hemorrhage or other forms of shock, even in semi-austere treatment settings that lack access to fluoroscopy. This technology also offers a much less invasive and viable alternative to current procedures for arresting hemorrhage, such as thoracotomy. Once the arterial occlusion balloon is inflated, blood pressure to the lower extremities and less critical organs is reduced, while blood pressure to the brain and heart is increased, thereby supporting the vital functions of life while corrective actions can be taken.

As used herein, the terms proximal and distal are from the perspective of the physician or other medical professional, such that proximal describes a direction away from a patient, while distal describes a direction toward the patient.

The self-centering endovascular wire of the present disclosure is biocompatible and is provided with calibration indicia, such as major length markers in 5 cm increments and minor length markers in 1 cm increments along the shaft. The J tip is provided at a leading (distal) end of the self-centering endovascular wire to prevent vessel perforation as the wire is advanced along the torso arterial tree toward the thoracic aorta.

Immediately below (i.e., just proximately of) the J tip, four self-expanding nitenol wire projections are provided encircling the endovascular wire, which can move along the endovascular wire as they expand or contract. Two beads are provided to anchor the four self-expanding projections relative to the endovascular wire, with one of the beads at a leading or distal end of the four self-expanding projections, and the other of the beads at the trailing or proximate end of the four self-expanding nitenol wire projections. The beads are of a diameter sufficiently small to pass through the transdermal or percutaneous sheath, yet large enough to prevent movement of an arterial occlusion balloon, delivered on the endovascular wire, past the four self-expanding nitenol wire projections.

The transdermal or percutaneous sheath, by way of example, may be a 6 French sheath having a length of about 10 cm. Upon insertion and advancement of the percutaneous sheath into the femoral artery at the femoral head, the distal outlet end of the sheath is open to an interior of the external iliac artery. When inserted into the sheath, the four self-expanding nitenol wire projections of the self-centering endovascular wire are in their unexpanded state. Each of the nitenol wires has a diameter of approximately 0.014 inch. When advanced outside the sheath into the external iliac artery, each of the four nitenol wire projections reacts to human body temperature and expands, until the strut portion (between the anchoring beads) reaches an overall cross-sectional dimension within a range of about 5 mm to as much as about 25 mm, with the wire projections opposing the arterial wall in all directions. The expanded state of the wire projections causes the shaft of the lead portion of the endovascular wire to be centered in the arterial lumen, helping prevent the endovascular wire from inadvertently diverting into an undesired arterial branch, such as the kidney arteries arising from the abdominal aorta, along the course of its travel toward the thoracic aorta inferior to the left subclavian artery. The thermal expansion of the four nitenol wire projections, or struts, is a reversible process, such that when it is desired to remove the endovascular wire from the patient, the four nitenol wire projections can be re-constrained or collapsed as they re-enter the transdermal sheath.

The aortic occlusion balloon includes a 2-lumen hollow balloon shaft. The distal lumen extends the length of the catheter, including a tapered tip to prevent the balloon from passing over the proximal bead anchor of the self-centering nitenol wire strut mechanism on the self-centering endovascular wire. The balloon shaft may include pre-calibrated length markers. The other lumen communicates with the balloon and is used to expand and deflate the balloon. A terminating port with a one-way valve may be provided to be engaged by a fluid source, such as a syringe, for selective inflation and deflation of the arterial occlusion balloon. A pressure gauge may be provided in communication with the valve at the terminating port, which may be calibrated to alert the physician when sufficient pressure has been attained to adequately inflate the aortic occlusion balloon. The self-centering wire and occlusion balloon may be inserted as a single unit or device.

In another aspect of the disclosure, an apparatus and method of determining endovascular insertion lengths and diameters based upon external torso anatomy without the use of fluoroscopy is provided. The apparatus and method are particularly useful in emergency, intensive care unit, or surgical environments where apparatus insertion into the vascular tree, be it arterial or venous, has been dependent upon fluoroscopy that is now not readily available.

In such emergency settings, for example, vascular lengths may be estimated based on carefully prescribed algorithms that correlate these average vascular lengths and diameters for men and women to external torso extent, e.g., the distance between the sternal notch to the symphisis pubis. This distance can be easily measured by drawing an extendible tool, such as a tape or telescoping measuring device, across a patient's body and holding the tool between these two external points of torso measurement.

BRIEF DESCRIPTION OF THE SEVERAL VIEWS OF THE DRAWINGS

FIG. 1A is an anatomical representation of a human body, illustrating consistently identifiable external boney landmarks of the torso;

FIG. 1, illustrates hollow needle entry into the left common femoral artery at the femoral head to allow first placement of a wire through the hollow needle into the common femoral artery in the direction of the external iliac artery or torso, and then, after removal of the needle from over the wire, placement of a transdermal sheath over the wire and into the artery, establishing a working port within the lumen of the blood vessel;

FIG. 6 is a perspective view of the self-centering endovascular wire with an arterial occlusion balloon disposed proximally of the self-centering nitenol wire struts, illustrating the arterial occlusion balloon in an uninflated condition;

FIG. 7 is a plan view of the self-centering endovascular wire and arterial occlusion balloon of FIG. 6 in an implanted and inflated condition within the thoracic aorta, inferior to the left subclavian artery;

FIG. 15 is a front perspective view of an exemplary torso vascular insertion tool;

FIG. 16 is a back perspective view of the exemplary torso vascular insertion tool;

FIG. 18 is a front perspective view of the second embodiment of the exemplary torso vascular insertion tool having a cover disposed thereon.

DETAILED DESCRIPTION OF THE PREFERRED EMBODIMENTS

Figures 1, 2:
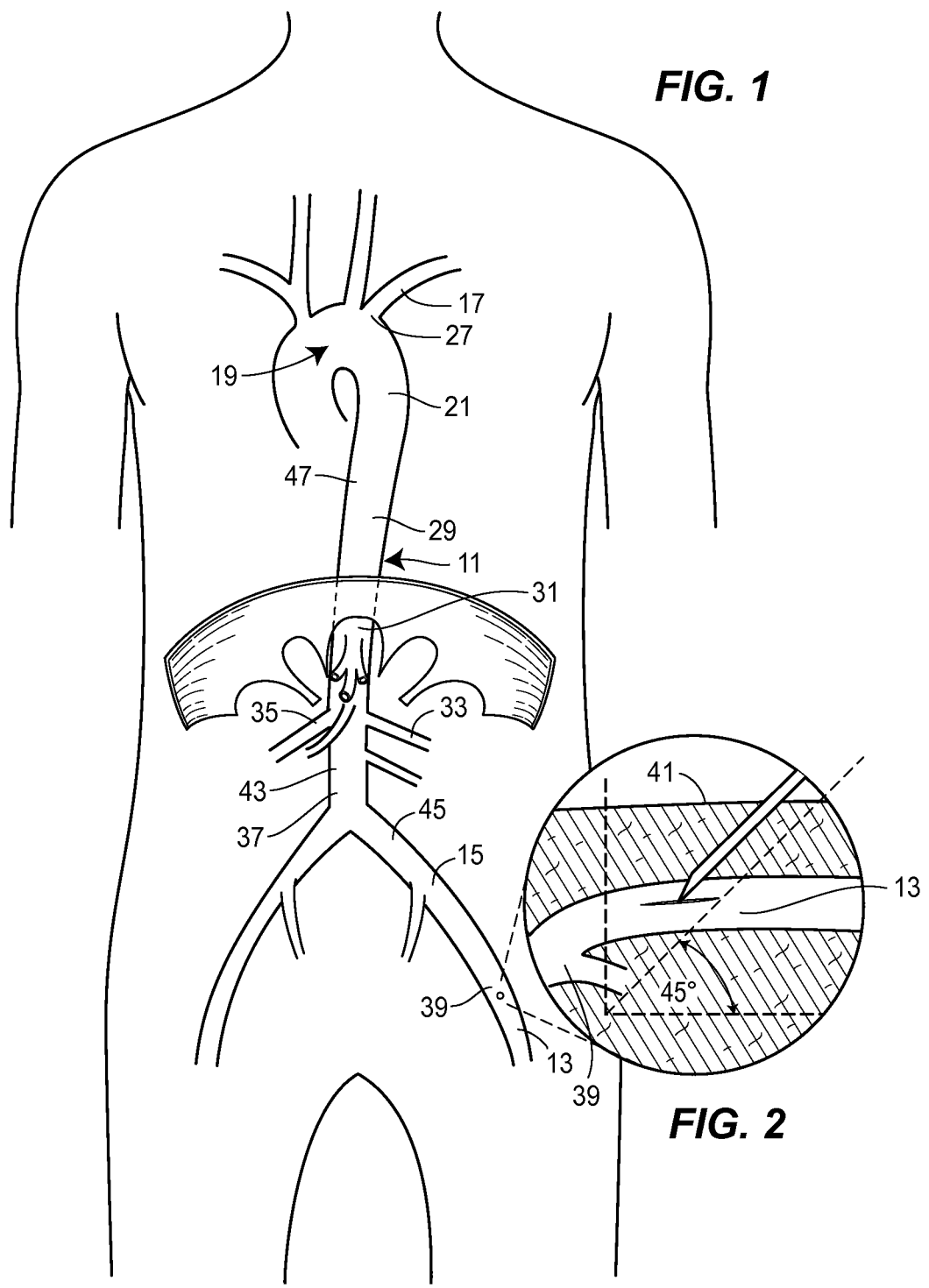
FIG. 1 is an anatomical representation of a human body, illustrating the arterial path from the common femoral artery to the thoracic aorta, inferior to the left subclavian artery at the aortic arch.
FIG. 2, embedded within

A thoracic aortic occlusion system 10 of the present disclosure is illustrated in FIG. 6. This thoracic occlusion system 10, and method of using the same, employs correlation data extracted from a statistically reliable pool of human patients. As used herein, even reference numerals denote structural features of the thoracic aortic occlusion system 10, while odd reference numerals denote anatomic locations of a human. The system 10 relies upon this data to predict the arterial measurement of a normal torso arterial tree 11 from the femoral artery 13 at the level of the femoral head 15 to a level just below 21 the left subclavian artery 17 at the aortic arch 19 (or other relevant locations), each of which is illustrated in FIG. 1. Using this prediction model or nomogram, a trained medical professional can derive the distance to which a calibrated, self-centering endovascular wire 12 of the present disclosure should be advanced from the femoral artery 13 into the descending thoracic aorta 29 to a level just below 21 the left subclavian artery 17 and the aortic arch 19 before deploying an occlusion balloon 14 (FIG. 6) over this endovascular wire 12 to the same position. More specifically, the occlusion balloon 14 is deployed at a location 21 inferior of the left subclavian artery 17 at the aortic arch 19, in an effort to augment or support heart and brain profusion in the setting of end-stage shock resulting from non-compressible torso hemorrhage.

The prediction model or nomogram may be developed from, by way of example, a population of male and female trauma patients between the ages of 18-45 years. Computed tomographic measurements are made from the pool of patients to develop statistical associations between distances separating consistently located, external anatomical or boney landmarks and measurements (namely length and diameter data) within the central vascular anatomy.

A first anatomical landmark distance measured for each patient is a torso extent (in cm), from the symphysis pubis 23 to the sternal notch 25, as illustrated in FIG. 1A. Center-line measurements are also taken (in cm) from the femoral artery 13 at the level of the femoral head 15 to the left subclavian artery 17. These measurements are supplemented with center-line measurements (in cm) from the femoral artery 13 at the level of the femoral head 15 to seven additional key points of anatomical interest, including: (a) the left subclavian artery origin 27; (b) the artery of Adamkiewics origin 29; (c) the celiac artery origin 31; (d) the left renal artery origin 33; (e) the right renal artery origin 35; (f) the aortic bifurcation 37; and (g) the iliac artery bifurcation 39. In addition to measuring the center-line distance from the femoral artery 13 at the level of the femoral head 15 to these various locations, cross-sectional diameter (in mm) and cross-sectional area (in $mm^2$) measurements are also determined for each respective vessel. A measurement is also taken of the distance (in mm) a hollow tip access needle would traverse at a 45° insertion angle from the epidermis layer of the skin 41 to an initial entry point of the femoral artery 13, which may be referred to as a percutaneous access length measurement.

For each of the measurements described above, data is collected and means, standard deviations, and $95^{th}$ % confidence intervals are calculated, by gender, for minimum, maximum, 1st, $5^{th}$, $10^{th}$, $25^{th}$, median, $75^{th}$, $90^{th}$, $95^{th}$, and $99^{th}$ percentiles. Based on these calculations, a mathematical model employing height and gender as covariates defining the statistical association between the external measure of torso extent (i.e., distance from the symphysis pubis 23 to the sternal notch 25) and the central vasculature anatomy data is created. This mathematical model or nomogram may be the basis for a conversion chart that a medical professional, unaided by fluoroscopic guidance (i.e. fluoroscopy-independent), may use to calculate the proper insertion distance of the calibrated endovascular wire 12 of the thoracic aortic occlusion system 10 for a given patient.

Figure 3:
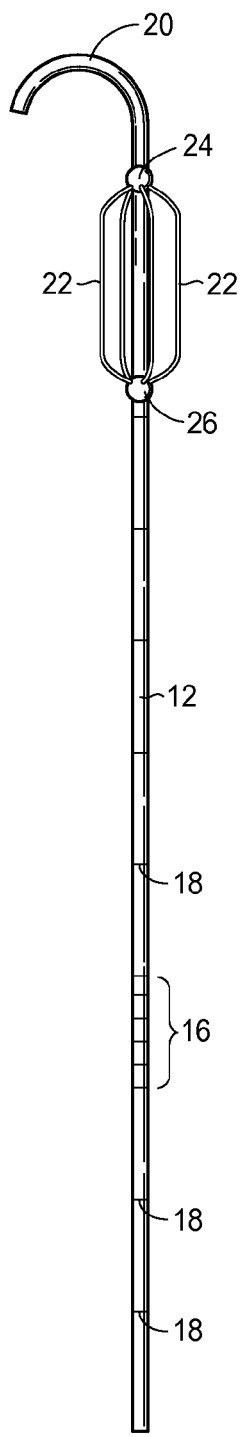
FIG. 3 is an enlarged plan view of a self-centering endovascular wire of the present disclosure.

Turning now to FIGS. 3-11, the thoracic aortic occlusion system 10 is illustrated. Referring now to FIG. 3, the system includes a self-centering endovascular wire 12, preferably made of a biocompatible wire having calibration indicia thereon, such as pre-calibrated minor length markers 16 provided at 1 cm intervals, and major length markers 18 provided at 5 cm intervals along the length of the self-centering endovascular wire 12. By way of example, the overall length of the self-centering endovascular wire 12 may be 180 cm and have a diameter of approximately 0.035 inch. The self-centering endovascular wire 12 includes a J tip 20 at a distal end thereof. The J tip 20 is used to minimize trauma to or perforation of the arterial vessels as the endovascular wire 12 is advanced along the torso arterial tree 11. The J tip 20 is also sufficiently flexible to unfold in the event the J tip 20 was to hook onto an arterial branch, such as during withdrawal of the endovascular wire 12.

Immediately proximate of the J tip 20 is a plurality of self-expanding wire struts 22. The wire struts 22 extend between a leading securement bead 24 and a trailing securement bead 26, both of which secure the wire struts 22 to the endovascular wire 12. The self-expanding wire struts 22 are made of a material that expands upon exposure to fluid at body temperature, such as nitenol, and are disposed at sufficient intervals about the endovascular wire 12, such as four self-expanding wire struts 22 at 90° intervals. These struts 22, when in their collapsed state such as during insertion through a transdermal sheath 28, will span the length of the securement beads 24 and 26. However, the struts 22 will shorten in the length as they extend over the endovascular wire 12 when in their expanded state, such as within the descending thoracic aorta 21, and as such the wire struts 22 will be movable to some extent axially relative to the endovascular wire 12, but between the securement beads 24 and 26. In this manner, the self-expanding wire struts 22 serve a self-centering function, keeping the tip or leading end of the endovascular wire 12 away from the sidewalls of the arterial vessels, helping to prevent the endovascular wire 12 from turning down an unintended branch. For example, the left renal artery origin 33 (FIG. 1), the right renal artery origin 35 (FIG. 1), and the celiac artery origin 31 (FIG. 1) each can branch off from the abdominal aorta 43 at a 90° angle thereto. The nitenol self-expanding wire struts 22 serve to maintain the endovascular wire 12 within the abdominal aorta 43 (FIG. 1).

Figure 4:
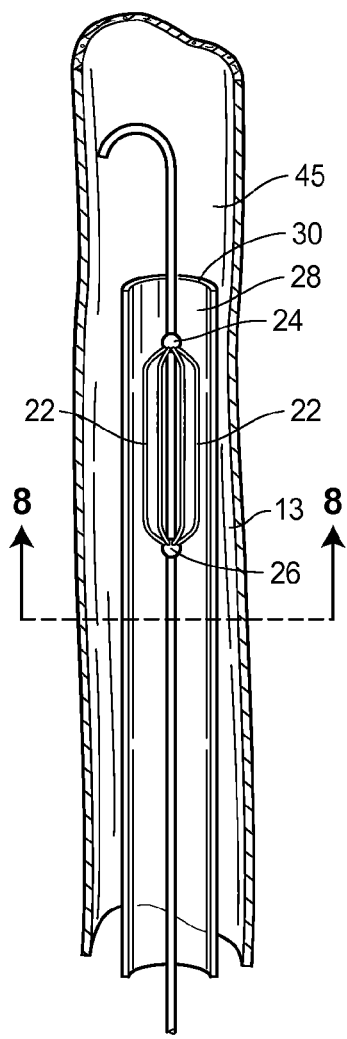
FIG. 4 is a perspective view of the self-centering endovascular wire of FIG. 3 as it is extended in its constrained or collapsed form through a transdermal sheath from the femoral artery into the external iliac artery.
Figure 5:
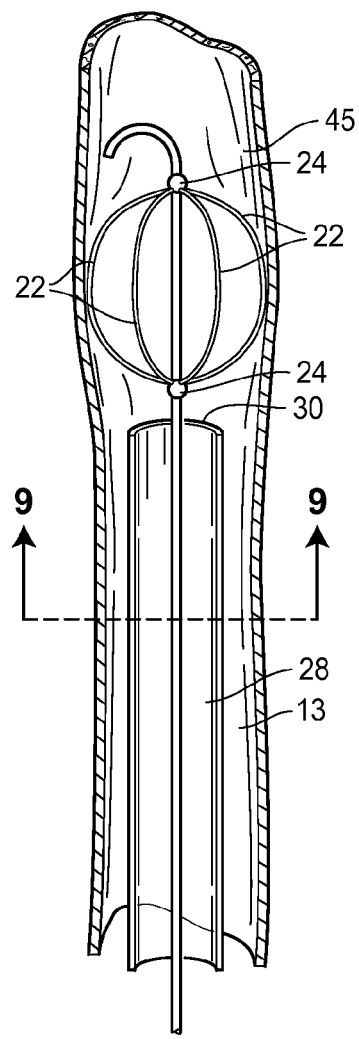
FIG. 5 is a perspective view of the thermally-activated self-centering endovascular wire and transdermal sheath similar to FIG. 4, illustrating the self-centering nitenol wire struts on the endovascular wire in an expanded condition or form after exiting the transdermal sheath within the external iliac artery.
Figure 8:
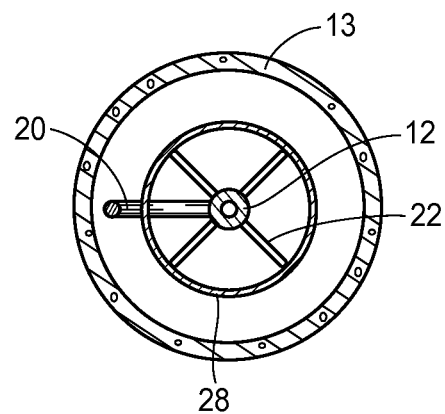
FIG. 8 is a cross-sectional view, taken along lines 8-8 of FIG. 4.
Figure 9:
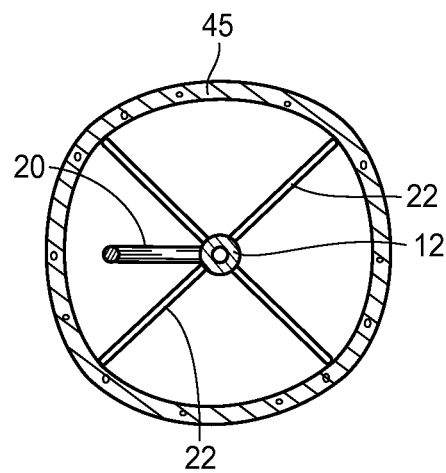
FIG. 9 is a cross-sectional view, taken along lines 9-9 of FIG. 5.

Referring now to FIG. 4, a transdermal or percutaneous sheath 28, preferably 6 French, and by way of example having a length of approximately 10 cm with an inner diameter of approximately 0.087 inches is illustrated. The sheath 28 is inserted into the femoral artery 13 through a puncture in the skin 41 (FIG. 2) with a hollow tip needle to provide an access port by way of first a wire and then the sheath 28. The distal end 30 of the sheath 28 is positioned within the external iliac artery 45 (FIG. 1).

The endovascular wire 12, the J tip 20, the leading securement bead 24, the trailing securement bead 26, and the unexpanded occlusion balloon 14 (which is disposed proximate to the trailing securement bead 26 and illustrated in FIG. 6) are all of sufficiently small cross-sectional dimensions to pass through the sheath 28. The leading securement bead 24 and the trailing securement bead 26 are also of a sufficient diameter so as to prevent the occlusion balloon 14 from migrating distally over the wire struts 22 and past the J tip 20.

Referring now to FIG. 6, the aortic occlusion balloon 14 is carried on a balloon shaft 32 having pre-calibrated length indicia 34 thereon. The pre-calibrated length indicia 34 may include minor length markers 34a in 1 cm increments, and major length markers 34b in 5 cm increments. The balloon shaft 32 preferably has a length of approximately 90 cm (35.43 inches) and an outer diameter less than approximately 1.98 mm (0.087 inches), so as to fit through the sheath 28. The balloon shaft 32 includes a lumen 42 (see also FIGS. 10 and 11), permitting the balloon shaft 32 to pass over the endovascular wire 12. A tapered distal end portion 44 of the balloon shaft 32 prevents the balloon shaft 32 from being inserted past the trailing securement bead 26. The balloon shaft 32 will remain over the self-centering endovascular wire 12 during occlusion balloon inflation to provide a rigidity that is sufficient to permit the balloon to be manually maintained at a desired location within the thoracic aorta 47 (FIG. 1), resisting distal or caudal migration, such as might otherwise result from aortic pulsation.

The aortic occlusion balloon 14 has a length of approximately 3 cm, and is affixed to the end of the balloon shaft 32 less than 1 cm below (proximally of) the tapered distal end portion of the balloon shaft 44. As indicated above, the aortic occlusion balloon 14 is inserted (in a collapsed state) through the transdermal or percutaneous sheath 28 with the endovascular wire 12 and the balloon shaft 32.

Upon navigating the endovascular wire to the desired location within the thoracic aorta 47, an inflation fluid is introduced through the balloon shaft 32 to the aortic occlusion balloon 14, causing the aortic occlusion balloon 14 to inflate, as illustrated in FIG. 7. By way of example, the aortic occlusion balloon 14 may, upon inflation to approximately 1 atm, expand to a maximum diameter of approximately 26 mm, conforming to the shape of the thoracic aorta 47, thereby obstructing blood flow through the thoracic aorta 47 inferiorly of the inflated aortic occlusion balloon 14 and promptly augmenting heart and brain profusion. The inflation fluid is a sterile biocompatible fluid introduced to the multi-port and valve assembly 36 (FIGS. 10 and 11) using a fluid source, such as a syringe 48. Upon removal of the sterile inflation fluid, the aortic occlusion balloon 14 deflates, permitting withdrawal thereof through the transdermal or percutaneous sheath 28.

Figure 10:
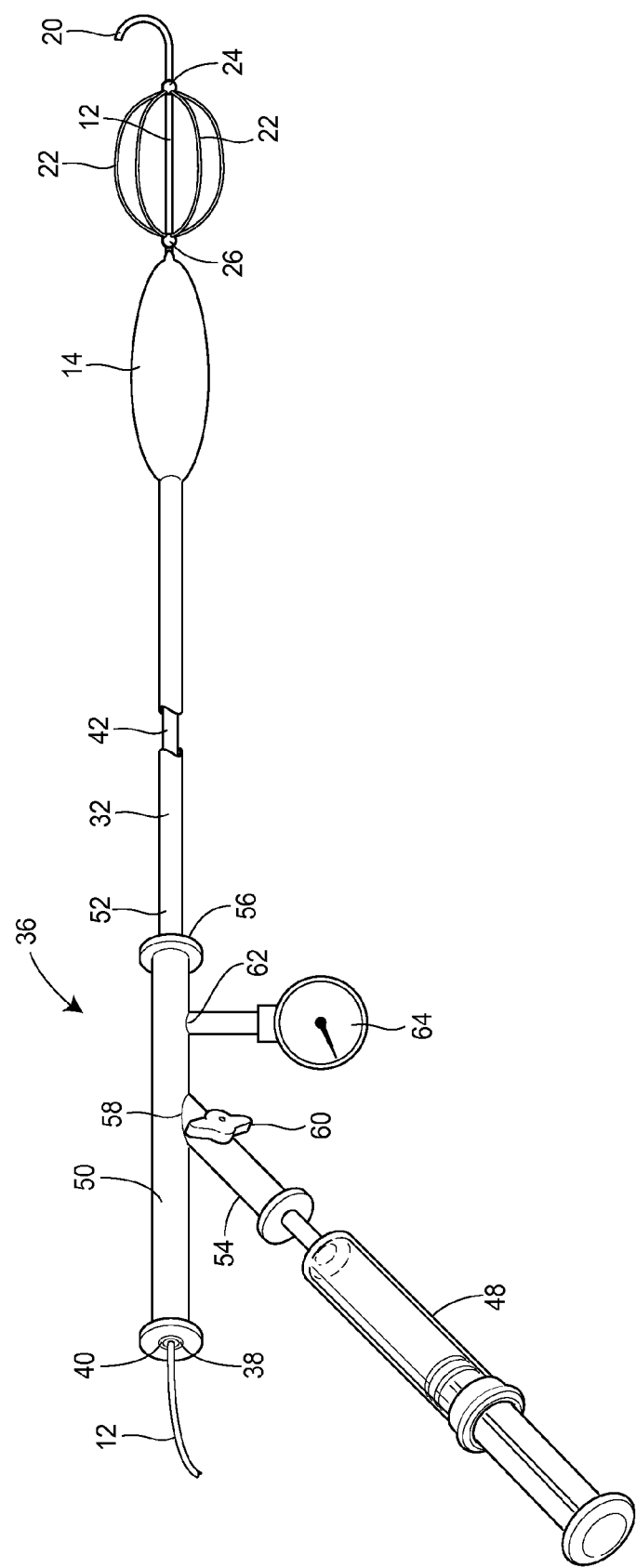
FIG. 10 is a perspective view of a multi-way port affixed to a balloon shaft of the arterial occlusion balloon of FIG. 6, illustrating a one-way valve associated with a main port of the multi-way port in a closed position, preventing fluid communication between a fluid source, such as a syringe, and the balloon shaft and preventing the passage of an inflation medium through the port.
Figure 11:
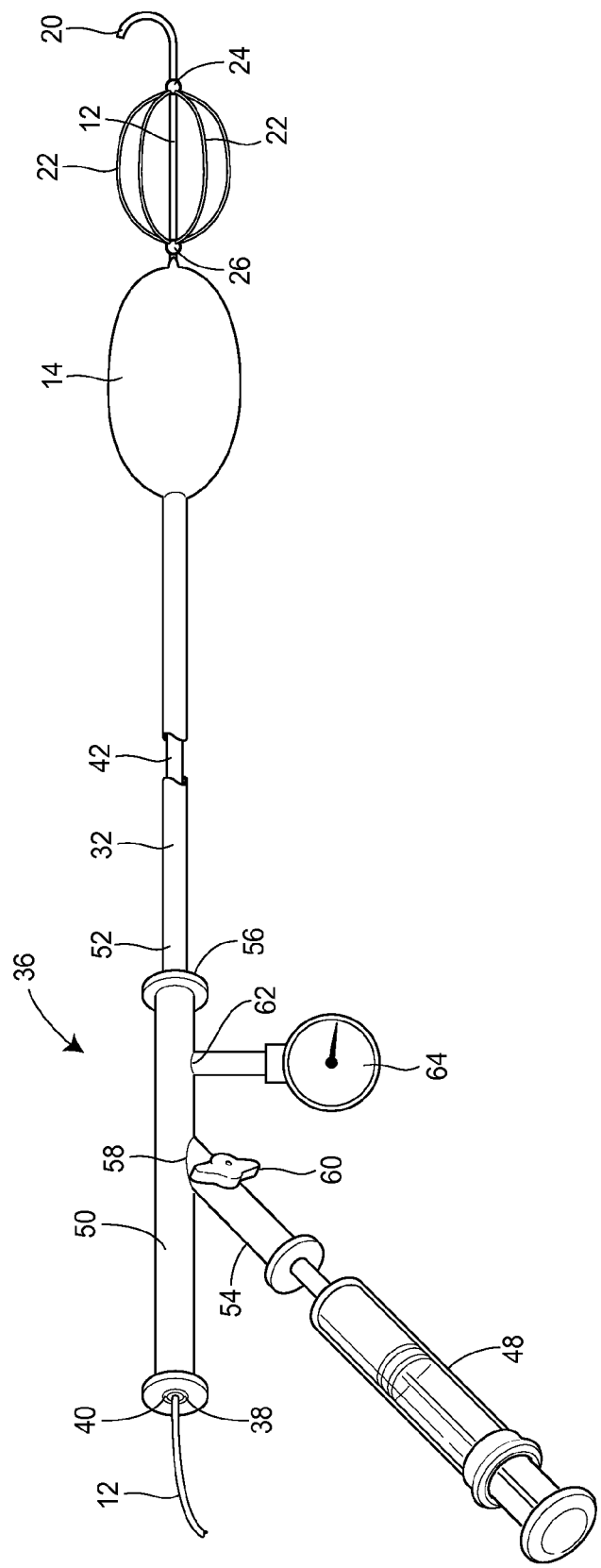
FIG. 11 is a perspective view of the multi-way port of FIG. 10, illustrating the one-way valve in an open position, permitting fluid communication between a fluid source, such as a syringe, and the balloon shaft to achieve inflation or deflation of the arterial occlusion balloon and an inflation medium through the port and into the balloon shaft.

As illustrated in FIGS. 10 and 11, the aortic occlusion balloon 14 is inflated and deflated via a multi-port and valve assembly 36. The multi-port and valve assembly 36 includes a one-way valve, which is preferably pressure gauge calibrated so as to alert a physician when the aortic occlusion balloon 14 has reached its desired inflation pressure. The multi-port and valve assembly 36 further includes a terminating port 38, with a diaphragm 40. The endovascular wire 12 can extend through the diaphragm 40, while maintaining fluid-tight communication between the multi-port and valve assembly 36 and the aortic occlusion balloon 14. The multi-way port and valve assembly 36 further includes an elongate tubular barrel section 50 affixed to a proximal end 52 of the balloon shaft 32. The elongate tubular barrel section 50 may have a length of approximately 10 to 15 cm. The elongate tubular barrel section 50 does not pass through the transdermal sheath 28 or enter the body of the patient. In addition to the terminating port 38, which may be considered a first port, the multi-way port and valve assembly 36 includes a second port 56 at a distal end. As discussed above, the multi-way port and valve assembly 36 further includes a diaphragm 40, which is disposed at a proximal end of the elongate tubular barrel section 50. The diaphragm 40 permits the endovascular wire 12 to pass through and extend externally of the first port 38, while maintaining a fluid-tight connection, thereby avoiding leakage of bodily fluid through the first port 38.

A side port 58 and a branch 54 off the elongate tubular barrel section 50, intermediate the first port 38 and second port 56, enables attachment of the syringe 48 to the multi-way port and valve assembly 36. A one-way valve 60 is actuable between an open condition (permitting passage of inflation fluid therethrough), as illustrated in FIG. 11, and a closed condition (preventing passage of inflation fluid), as illustrated in FIG. 10. Preferably, the one-way valve 60 is in an open condition when oriented parallel to the branch 54 off the elongate tubular barrel section 50 (FIG. 11), and is in a closed condition when rotated to a position perpendicular to the branch 54. An additional port 62, provided intermediate the one-way valve and the proximal end 52 of the balloon shaft 32 to which the multi-way port and valve assembly 36 is affixed, is provided with a pressure monitoring device 64. A physician may monitor the pressure monitoring device 64 during inflation, enabling the physician to determine when the pressure within the occlusion balloon 14 and the balloon shaft 32 has reached a pressure of, for example, 2 atm, so as to avoid over-inflation and potential injury to the thoracic aorta 47.

Using a correlation chart or nomogram derived from the statistical data regarding the measurements between the consistently identifiable external measures or landmarks of torso extent (e.g. the symphysis pubis 23 and the sternal notch 25), the physician calculates the proper distance to which the endovascular wire 12 and balloon shaft 32 are to be inserted into the transdermal sheath 28 through a puncture in the skin 41 and into the femoral artery 13 at the location of the femoral head 15, thereby positioning the aortic occlusion balloon 14 at the desired location 21 within the thoracic aorta 47, inferiorly of the left subclavian artery 17 without the aid of fluoroscopy (i.e. fluoroscopy-independent). The major length markers 18 along the endovascular wire 12 may be annotated with length-identifying numbers to facilitate determination of the length to which the self-centering endovascular wire 12 has been advanced within the torso arterial tree 11. Upon insertion to the desired length, with the one-way valve 60 in the open condition, the physician actuates a piston of the syringe 48, thereby introducing inflation fluid through the balloon shaft 32 and into the occlusion balloon 14, inflating the occlusion balloon 14 to a volume sufficient to block the thoracic aorta 47.

The endovascular, fluoroscopy-independent resuscitative thoracic aortic occlusion system 10 of the present disclosure may be provided to users in the form of a kit, enabling assembly of the same at, by way of example only, a forward surgical hospital close to a battlefield in a civilian trauma setting either outside of a hospital or in a resuscitation room of an emergency department. The system 10 may be applied in clinical scenarios other than traumas addressed in such urgent care settings, such as cardiac arrest, neurogenic shock, or postpartum hemorrhage that may occur in operating or delivery rooms. The kit may include the endovascular wire 12 having the J tip 20 and at least one wire strut 22 disposed proximally to the J tip 20. The kit may further include the occlusion balloon 14 that may be disposed proximally on the balloon shaft 32, and advanced over the endovascular wire 12 until it reaches the trailing securement bead 26. The transdermal sheath 28 may also be a part of the kit, such that the transdermal or percutaneous sheath 28 is able to receive each of the endovascular wire 12, the occlusion balloon 14 when in an uninflated condition, and the balloon shaft 32, as described above. When assembled with the endovascular wire 12, the balloon shaft 32, and the transdermal sheath 28, the occlusion balloon 14 may be selectively inflated and deflated at a desired location within the thoracic aorta 47 of a patient to treat vascular injury without the aid of fluoroscopy.

The kit may further include the multi-port and valve assembly 36 in fluid communication with both the proximal end of the balloon shaft 32 and a fluid source, such as the syringe 48, as also described above. One of a table, a nomogram, a chart or a graph correlating distances between at least readily externally identifiable anatomical landmarks of a pool of humans to distances from the femoral artery 13 to a location within the thoracic aorta 47 to which the endovascular wire 12 and the balloon shaft 32 are to be inserted may also be included in the kit.

Figure 12:
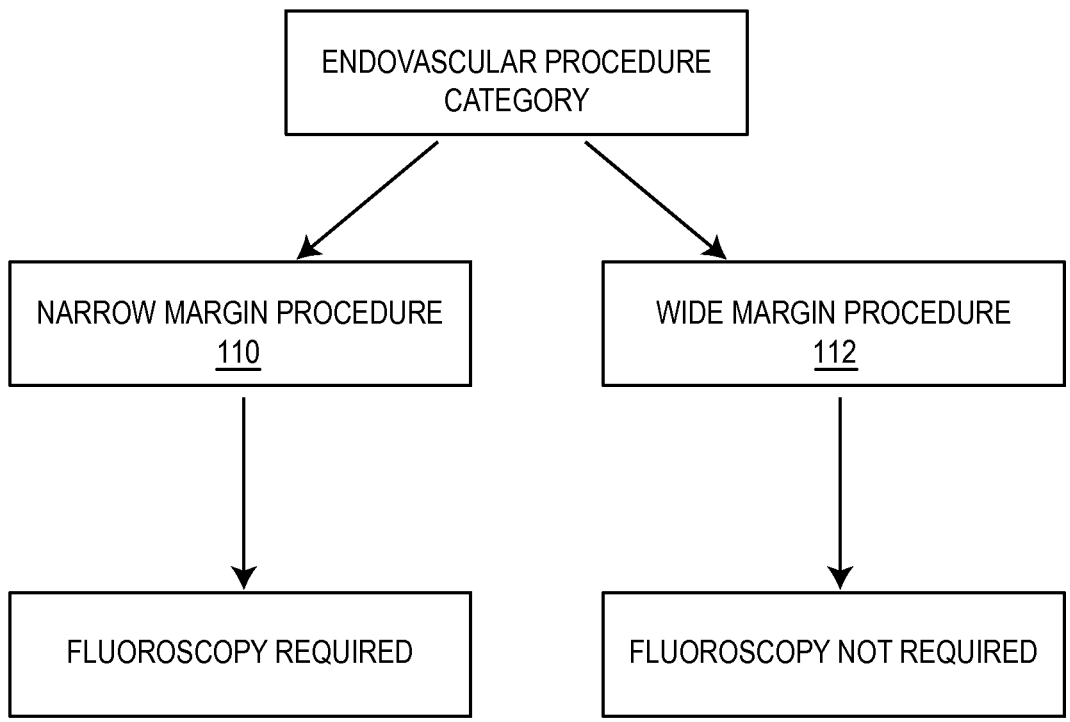
FIG. 12 is a flow chart illustrating endovascular procedure categories in large axial vessels of a human torso.

Referring now to FIGS. 12-18, additional embodiments of the present disclosure are illustrated. Referring to FIG. 12, endovascular procedures in large axial vessels of the human torso may be considered as narrow margin procedures 110 or wide margin procedures 112. In other words, many catheter-based procedures in the aorta and vena cava require exact positioning of devices to be safe and effective, and, therefore, have a narrow margin of error during procedures. The narrow margin procedures 110 require standard fluoroscopy to effectively and accurately direct the procedure. Examples of narrow margin procedures 110 include: (1) placement of stent grafts to treat age-related aneurysms near major branch vessels of the thoracic or abdominal aorta; or (2) treatment of local or localized disease processes such as arterial stenoses caused by atherosclerosis with balloon angioplasty and bare metal stents. Because these procedures entail placing devices at the exact location, i.e., within millimeters, of vital branch or vein locations, they require real time visualization using contrast agents and fluoroscopy.

Other catheter-based endovascular procedures have a wider margin of error. Examples of wide margin procedures 112 include positioning of occlusion balloons to control torso hemorrhage, vena cava filter devices to prevent pulmonary embolus, and stent grafts to treat vessel disruptions localized by computed tomography (CT). In the case of balloon occlusion, the goal is to temporarily halt flow beyond a certain point in the vena cava or aorta to aid with hemorrhage control. Additionally, in the setting of aortic occlusion, life-preserving blood pressure above, or proximal to the balloon occlusion, is maintained or supported. In these instances, the balloon may be positioned anywhere over a much longer length of vessel, e.g., within several centimeters, prior to inflation. Similarly, positioning and placement of thromboembolic filter devices in the vena cava may occur over a relatively wide distance of vessel, e.g., between the iliac vein confluence and the renal veins. Thus, in such wide margin procedures, fluoroscopy is not required.

While fluoroscopy is not required, a detailed characterization of the axial vessels of the human torso is necessary to accomplish such procedures in fluoroscopy free environments. Contrast-enhanced computer tomography (CT) using 64-panel detectors and special measuring software allows for such detailed characterization. More specifically, software programs placed in or alongside CT units allow precise centerline measurements within the axial vessels as well as determination of their diameter. Application of centerline measurements allows definition of clinically relevant distances between a standard vascular entry point, i.e., femoral vessels and major branch artery points within the vessels.

Referring back to FIG. 1, the normal torso arterial tree 11 with major branch artery points is illustrated. The major branch artery points include a left femoral artery 13, an external iliac artery 45, and a left subclavian artery 17. Center-line measurements are taken (in cm), for example, from the femoral artery 13 at the level of the femoral head 15 to the left subclavian artery 17, as the left femoral artery 13 is a common vascular entry point. As also illustrated in FIG. 1, other major branch artery points include the artery of Adamkiewics origin 21, the celiac artery origin 31, the left renal artery origin 33, the right renal artery origin 35, the aortic bifurcation 37, and the iliac artery bifurcation 39. In addition to measuring the center-line distance from the femoral artery 13 at the level of the femoral head 15 to these various locations, cross-sectional diameter, e.g., in mm, and cross-sectional area, e.g., in mm2, measurements are also determined for each respective vessel.

Figure 13:
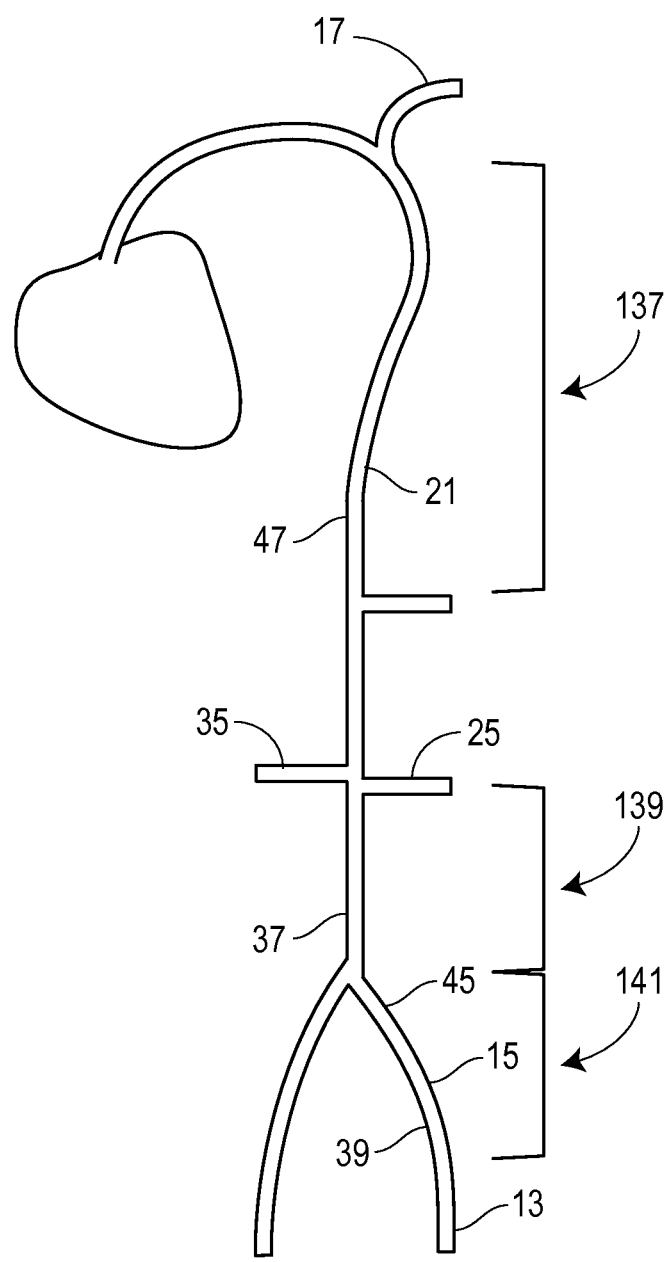
FIG. 13 is an anatomical representation of the human body, illustrating arterial torso vascular anatomy.

Referring now to FIG. 13, arterial torso vascular anatomy is illustrated with various landing zones within the thoracic aorta 47 for wide margin procedures 112. For example, a thoracic aortic zone 137 is disposed below a region adjacent to the left subclavian artery 17 along a descending thoracic aorta 47. An infrarenal aortic zone 139 is disposed between left renal artery 25 and the iliac artery 45, and a common iliac artery zone 141 is disposed between the aortic bifurcation 37 and a distal end of the femoral artery 13.

Figure 14:
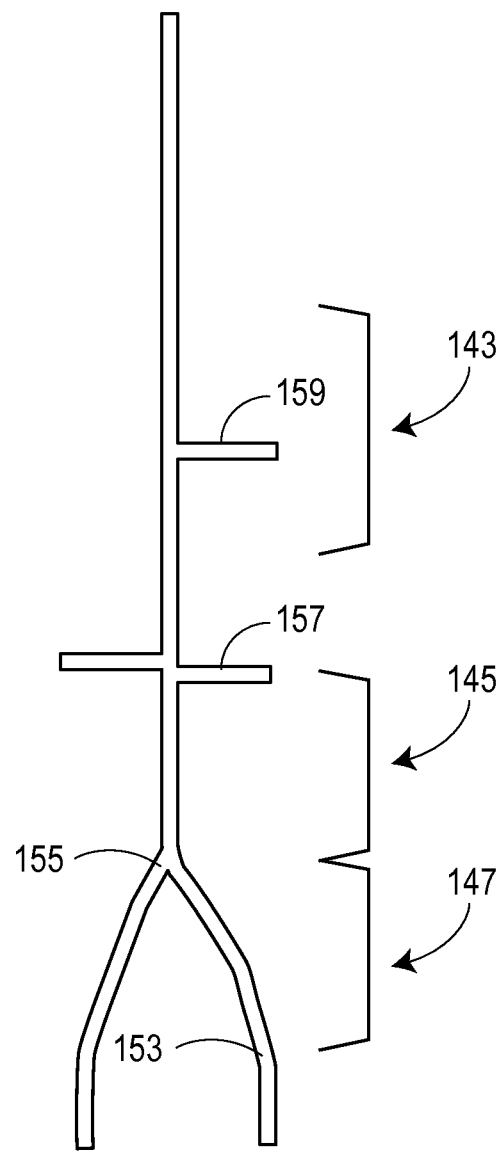
FIG. 14 is another anatomical representation of the human body, illustrating venous torso vascular anatomy.

Referring now to FIG. 14, venous torso vascular anatomy is illustrated with various landing zones within the vena cava for wide margin procedures. For example, a retro-hepatic inferior vena cava zone 143 is disposed along a descending thoracic aorta 47. An infrarenal IVC zone 145 is disposed below the retro-hepatic inferior vena cava zone 143, and a common iliac vein zone 147 is disposed below the infrarenal IVC zone 145.

To further characterize torso vascular morphometry, it is necessary to account for the relationship between vascular lengths and diameters and an individual's length or height. Because patient height is not consistently available, especially in the context of emergencies or trauma, an external measure of torso extent is needed.

Referring back now to FIG. 1A, an external measure of torso extent is illustrated. This measure extends from a sternal notch 25 to the symphisis pubis 23 and can be readily palpated and recorded, even in emergency and trauma settings. Not only is the external measure of torso extent readily available, but it provides a measure which is specific to the torso that houses vascular anatomy of interest.

Determination of vascular lengths or distances within the torso from a readily available external measure of torso extent requires correlation of this data to form a nomogram. The nomogram defines, with a predetermined confidence interval, the relationship between the external measure of torso extent and distances within the axial vessels of the torso, as well as the specific vessel diameters. If considered from the perspective of a common vascular entry point such as the femoral vessels, to clinically important branch points or landing zones 137-147 within the aorta or vena cava, the nomogram is relevant to the performance of wide margin endovascular procedures. The nomogram allows a provider to quickly estimate from a basic external measure, e.g., the distance between the sternal notch 25 and the symphysis pubis 23 (FIG. 1A), the distance from the femoral vessels to landing zones in the descending thoracic aorta 47 or the inferior vena cava.

Referring now to FIGS. 15 and 16, an exemplary torso vascular insertion tool 200 is illustrated. The tool 200 translates data from the above-described correlation and nomogram, making such information useful in a clinical setting. More specifically, and referring now to FIG. 15, a first side 210 of the tool 200 is illustrated. The first side 210 includes an edge 214 and a calibrated ruler 218 disposed on the edge 214 of the first side 210 for use in measuring a torso extent length, i.e., the length between the sternal notch 25 and the symphisis pubis 23 (FIG. 1A), on a patient. Adjacent to the calibrated ruler 218 on the first side 210 of the tool 200 is a first chart 220 providing a listing, by way of example, of male safe zone arterial insertion lengths from the femoral artery 13 vessels to relevant landing zones within the aorta. Such landing zones include the thoracic aortic zone 137, the infrarenal aortic zone 139, and the common iliac artery (CIA) zone 141. Adjacent to the first chart 220 disposed on the first side 210 of the tool 200 is a second chart 222. The second chart 222 provides a listing, by way of example, of male safe zone venuous insertion lengths from the femoral artery 13 vessels to relevant landing zones within the vena cava. Such landing zones include the retro-hepatic inferior vena cava (IVC) zone 143, the infrarenal IVC zone 145, and the common iliac vein (CIV) zone 147. For the torso arterial segment, the tool 200 provides distances from the femoral artery 13 to the aortic bifurcation 37, the lowest renal artery 33, the celiac artery 31, and the left subclavian artery 17 (see FIGS. 1 and 13). Venous insertion distances are provided from the femoral vein 153 to the bifurcation of the vena cava 155, the lowest renal vein 157, and the hepatic vein 159 (see FIG. 14).

Referring now to FIG. 16, a second side 212 of the exemplary torso vascular insertion tool 200 is illustrated. The second side 212 includes an edge 216 and a calibrated ruler 218 disposed on the edge 216 also for use in measuring on a patient the external torso extent between the sternal notch 25 and the symphysis pubis 23 (FIG. 1A), but this time for a female patient. A third chart 224 is disposed adjacent to the calibrated ruler 218 on the second side 212 of the tool 200. The third chart 224 provides, by way of example, a listing of female safe zone arterial insertion lengths from the femoral artery 13 vessels to relevant landing zones within the aorta. Such landing zones also include the thoracic aortic zone 137, the infrarenal aortic zone 139, and the common iliac artery (CIA) zone 141. Adjacent the third chart 224 is a fourth chart 226. The fourth chart 226 provides, by way of example, a listing of female safe zone venuous insertion lengths from the femoral artery 13 vessels to relevant landing zones within the vena cava. Such landing zones include the retro-hepatic inferior vena cava (IVC) zone 143, the infrarenal IVC zone 145, and the common iliac vein (CIV) zone 147.

The second side 212 may also include a listing of the diameter of the torso axial vessels at clinically important locations. More specifically, the back side 212 of the tool 200 provides the diameter of the iliac artery 39, the thoracic aorta 47, for the torso axial vessels. The venous diameters include the iliac vein and infrarenal and suprarenal vena cava. The second side 212 may also include clinically relevant specifications for endovascular devices commonly used in wide margin endovascular procedures 112, such as compliant balloons, basic stent grafts, and vena cava filters.

While various numerical indices and zones are included in the exemplary tool 200, the tool 200 is but one example; actual devices could use different numerical indices and zones than those provided in the exemplary tool 200 and still be within the scope of the appended claims.

Figure 17:
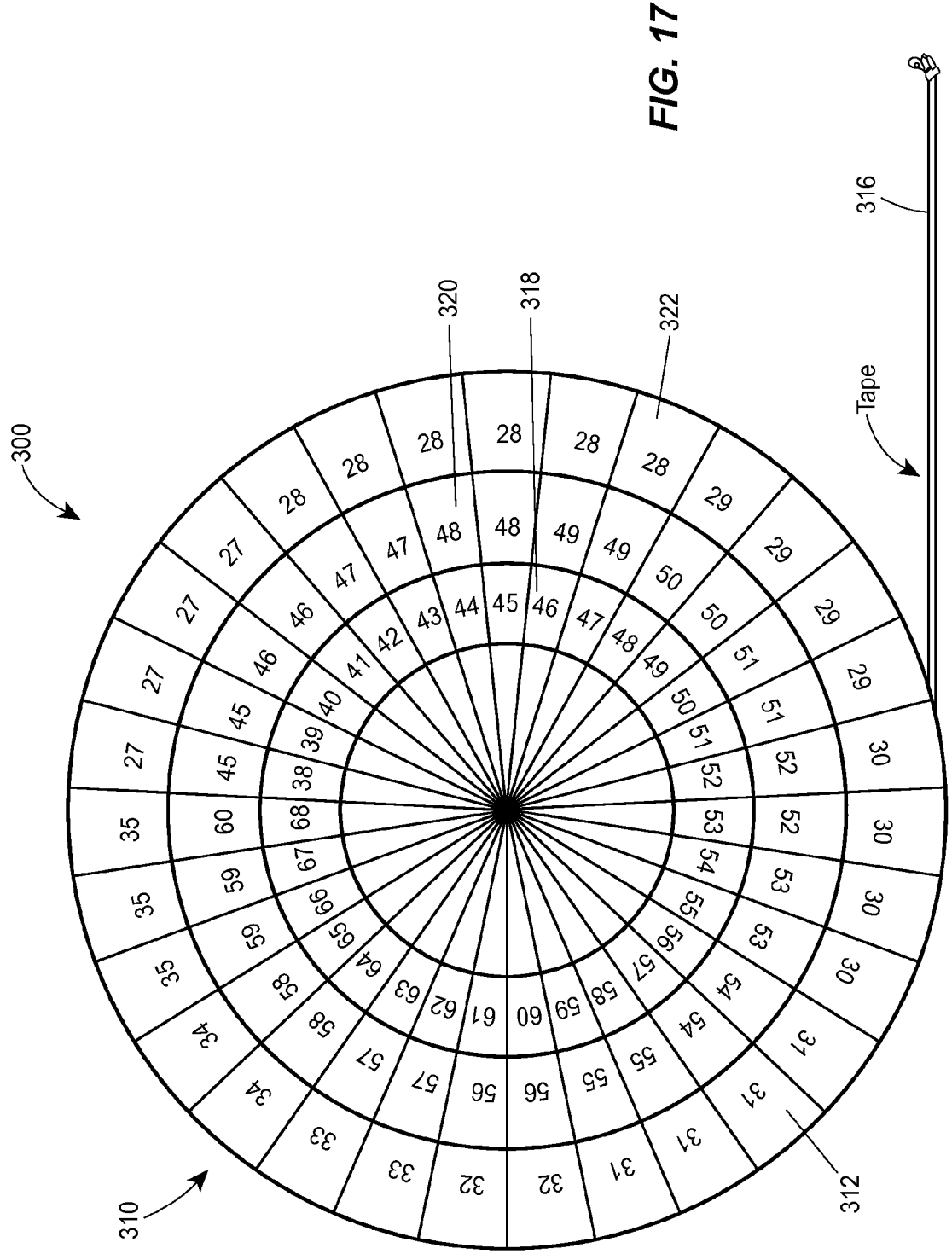
FIG. 17 is a front perspective view of a second embodiment of an exemplary torso vascular insertion tool.

Referring now to FIG. 17, a second embodiment of another exemplary torso vascular insertion tool 300 is illustrated. The torso vascular insertion tool 300 includes a data-wheel 310 having a first side 312, a second side (not shown) and a tape 316 wound between the first and second sides 312 of the data-wheel 310, a portion of the tape 316 extending along one side of the data-wheel 310. The tape 316 is used to measure on a patient the external measure of torso extent between the sternal notch 25 and the symphisis pubis 23 (FIG. 1A). By way of example, the first side 312 of the data-wheel 310 provides listings of male safe zone arterial insertion lengths from the femoral artery 13 vessels to relevant landing zones within the aorta corresponding to a circular listing of measured torso extent lengths. More specifically, the first side 312 of the data-wheel 310 includes an inner row 318, a middle row 320, and an outer row 322. The inner row 318 provides a circular listing of male torso extent lengths, e.g., in centimeters. The middle row 320 provides a circular listing of the thoracic aortic zone 137 lengths corresponding to the circular listing of male torso extent lengths; and the outer row 322 provides a circular listing of the infrarenal aortic zone 139 lengths also corresponding to the circular listing of male torso extent lengths. It will be understood by one of skill in the art that the first side 312 of the data-wheel 310 may alternatively provide listings of male safe zone venuous insertion lengths, for example. In addition, many other variations or combinations of correlation data between the measured torso extent length and new devices, different landing zones, and vessel sizes, for example, may also be provided on the data-wheel 310.

Referring now to FIG. 18, the second embodiment of the exemplary torso vascular insertion tool 300 is also illustrated, here with a cover 324 over the first side 312 of the data-wheel 310 of the tool 300. After a user draws the tape 316 over a patient to measure the external measure of torso extent between the sternal notch 25 and the symphisis pubis 23 (FIG. 1A), the cover 324 of the data-wheel 310 rotates to a value of the measured torso extent length displayed on the inner row 318 of the data-wheel 310. The user is then able to compare the torso extent length measured or shown on the inner row 318 of the data-wheel to one or more of corresponding safe zones displayed on the middle row 320, e.g., the thoracic aortic zone 137 insertion length, or the outer row 322, e.g., the infrarenal aortic zone 139 insertion length of the data-wheel 310 to calculate a length to which the endovascular device is to be inserted.

The second side (not shown) of the data-wheel 310 may include a circular listing of female safe zone arterial insertion lengths from the femoral artery 13 vessels to relevant landing zones within the aorta. Such landing zones also include the thoracic aortic zone 137, the infrarenal aortic zone 139, and the common iliac artery (CIA) zone 141. The second side of the data-wheel 310 may alternatively include a circular listing of female safe zone venous insertion lengths from the femoral artery 13 vessels to relevant landing zones within the vena cava. Such landing zones include the retro-hepatic inferior vena cava (IVC) zone 143, the infrarenal IVC zone 145, and the common iliac vein (CIV) zone 147.

Like the first side 312, the second side of the data-wheel 310 and tape 316 combination of the second embodiment of the torso vascular insertion tool 300 may be easily expanded or changed to alternatively include various other correlation data between the measured torso extent length and new devices and vessels sizes, for example.

While various numerical indices and zones are included in the exemplary tool 300, the tool 300 is also but one example; actual devices could use different numerical indices and zones than those provided in the exemplary tool 300 and still be within the scope of the appended claims.

Both embodiments of the torso vascular insertion tool 200, 300 may also include calipers or rods to facilitate measuring depending upon a patient's shape. More specifically, in patients having larger abdominal areas, the calipers or rods are needed to provide an accurate linear measurement of the patient's torso extent length because the larger abdominal areas would otherwise impede an accurate measurement. For example, when the torso vascular insertion tools 200, 300 are tape, and the tape is flexible and plastic, the caliper or rod may be disposed on one or both ends of the tape. The calipers or rods may also be retractable and extendible to help facilitate more accurate locating of externally-identifiable anatomic landmarks and measuring of the torso extent length in such patients.

While preferred embodiments of the present disclosure have been described above, variations may be made that are still within the scope of the appended claims.

What is claimed is:

1. A thoracic aortic occlusion system comprising:
   an endovascular wire;
   a balloon shaft comprising an aortic occlusion balloon on a distal end of the balloon shaft and a lumen to permit the balloon shaft to pass over the endovascular wire when the endovascular wire and the balloon shaft are inserted into a femoral artery at a femoral head of a patient; and
   a nomogram comprising one of a table, chart or graph correlating distances between at least two external anatomical landmarks of each human of a pool of humans to centerline distances from the femoral artery at the femoral head to a location within a thoracic aorta of each of the humans, where a distance between at least two anatomical landmarks is measured on a patient and compared to the distances between the at least two external anatomical landmarks on the nomogram to calculate a length to which the endovascular wire and the balloon shaft are to be inserted in the patient such that the aortic occlusion balloon is positioned at a desired location within the thoracic aorta without using fluoroscopy.

2. The system of claim 1, wherein the location within the thoracic aorta coincides with an aortic branch artery landmark.

3. The system of claim 1, wherein the location within the thoracic aorta is inferior to the origin of the left subclavian artery.

4. A method for deploying and selectively inflating a thoracic aortic balloon at a desired location within a thoracic aorta of a patient, comprising:
   measuring a distance between at least two readily externally identifiable anatomical landmarks of the patient, said anatomical landmarks including at least a symphysis pubis of the patient and a sternal notch of the patient;
   comparing the distance between the at least two external anatomical landmarks of the patient to a prediction model and calculating a length to which a calibrated endovascular wire and a balloon shaft of the thoracic occlusion system are to be inserted in the patient, the prediction model having correlation data for distances between the at least two external anatomical landmarks of torso extent of a pool of humans to centerline distances from a femoral artery at a femoral head to a location within the thoracic aorta of humans, the data measured using CT imaging; and
   inserting the calibrated endovascular wire and the balloon shaft to the length calculated for the patient independent of fluoroscopy.

5. The method of claim 4, wherein the prediction model is one of a table, a chart, a graph, or a nomogram.

6. The method of claim 4, wherein the method further includes pre-securing the balloon shaft to the endovascular wire proximate a trailing securement bead, allowing the balloon shaft and the endovascular wire to be inserted in the patient and delivered as a single unit.

\* \* \* \* \*